United States Patent [19]

Correa et al.

[11] Patent Number: 5,490,847
[45] Date of Patent: Feb. 13, 1996

[54] DISPOSABLE SANITARY NAPKIN

[76] Inventors: Mauro F. C. Correa, Av. Higienópolis, no. 101, 140 andar, São Paulo, SP; Telma Sinicio, Rua Jornalista Napoleão, Monteiro, no. 691; Fernanda S. Achcar, Av. Tivoli, no. 423, apto. 203, both of São José dos Campos, SP, all of Brazil

[21] Appl. No.: 156,191

[22] Filed: Nov. 22, 1993

[30] Foreign Application Priority Data

Nov. 25, 1992 [BR] Brazil .................................. 9204863

[51] Int. Cl.⁶ .................................................. A61F 13/15
[52] U.S. Cl. ............................................ 604/387; 604/385.1
[58] Field of Search ............................ 604/385.1, 385.2, 604/387, 358, 393, 397

[56] References Cited

U.S. PATENT DOCUMENTS

| | | | |
|---|---|---|---|
| 4,738,677 | 4/1988 | Foreman | 604/385.1 |
| 5,026,364 | 6/1991 | Robertson | 604/385.1 |
| 5,246,432 | 9/1993 | Suzuki et al. | 604/385.2 |
| 5,312,386 | 5/1994 | Correa et al. | 604/385.1 |

FOREIGN PATENT DOCUMENTS

| | | | |
|---|---|---|---|
| 5137750 | 6/1993 | Japan | 604/387 |
| 5220192 | 8/1993 | Japan | 604/387 |
| 2233235 | 1/1991 | United Kingdom | 604/385.1 |
| 9207536 | 5/1992 | WIPO | 604/385.2 |
| 9304651 | 3/1993 | WIPO | 604/387 |
| 9313736 | 7/1993 | WIPO | 604/387 |

*Primary Examiner*—Randall L. Green
*Assistant Examiner*—Rob Clarke

[57] ABSTRACT

The present invention provides a disposable intimate feminine absorbent with lateral regions or cuffs for containing liquids, which tend to assume a vertical position when the absorbent assumes, in use, an anatomical arched configuration.

20 Claims, 10 Drawing Sheets

DISPOSABLE SANITARY NAPKIN

The present invention relates to a disposable absorbent article and more specifically to an improved disposable intimate feminine absorbent as to leakage at the sides configured in such a way that along its length, there are regions having a liquid containing function.

For the purposes of this specification and the following claims the term disposable is to be understood to mean that the article is to be used only once after which it is rejected, without any possibility of washing or any other form of reusage.

It should also be understood that the term "intimate feminine absorbent" or "absorbent article" means an article to be used for collecting and containing vaginal exudates, typically menstrual blood, without however excluding, for example, intermenstrual secretions and even urine of incontinence.

One of the traditional problems of intimate feminine absorbent is leakage at the sides.

The causes of this phenomenon are innumerable, such as incorrect positioning of the absorbent article on the body or panties of the user, the incapacity of the article to absorb a large quantity of fluid discharged quickly onto its surface, the deformation of the absorbent core and/or of the structural elements of the absorbent article, etc.

PRIOR ART

The state of the art reveals prior attempts at solving such problems. One attempt appears in patient documents U.S. Pat. Nos. 4,015,604, 4,200,103 and EP391727 which disclose the placement of hydrophobic material close to the side edges of the absorbent core of intimate feminine absorbents, with a view to interrupting the course of liquids to the exterior of the article. Although efficient, such articles have less success in the event of large quantities of liquid discharge, when leakage occurs, not due to of failure of the absorbent core but to the slow removal of liquid present on the surface of the article in the direction to the absorbent material.

Another frequent attempt includes using the absorbent article with an arched conformation similar to that of a canoe and/or to raise the side wings in order to obtain physical barriers against the exit or lateral overflow of the liquid to the outside of the article; some examples are the U.S. Pat. Nos. 4,944,735, 4,701,177, 5,032,122, 3,570,493 and Brazilian Patent Application PI 8601228.

Yet another attempt to remedy such problem of lateral leakage is the use of flexible lateral tabs, commonly called "wings", which besides helping to fix the absorbent article to the panties of the user, when in use, also provide the conformation of lateral elevations which function as physical barriers against leakage—this being the argument contained U.S. Pat. Nos. 4,687,748 and 4,598,876. All of the solutions encountered in the prior art relate to improvements that reduce the problem of leakage, but without taking into account comfort, most of them failing to transmit visually to the user the impression of efficiency and assurance against such a problem.

It is, therefore, an object of the present invention to provide an intimate disposable feminine absorbent which partially or totally solves the problem of leakage and principally leakage at the sides, through the liquid containing regions.

Another object of the present invention is to provide an absorbent article which is at the same time efficient and comfortable for the user.

Still another object of the invention is to provide an absorbent article the contact of which with the crotch of the user is not uncomfortable.

Yet a further object of this invention is to provide an efficient absorbent article the manner of functioning of which is immediately perceptible to the user.

SUMMARY OF THE INVENTION

Such objects, and others related thereto, which will appear from a reading of this text, are obtained by the present invention which refers to a disposable intimate feminine absorbent article comprising:

- an upper liquid permeable sheet facing the user's body with which there is contact, with a view to receiving the liquid;
- a lower liquid impermeable sheet, opposite the upper sheet, in contact with the user's underclothes, serving as a lining for the absorbent article.
- a liquid absorbent core, located between the upper and lower sheets;
- at least one cuff along at least each side edge of the absorbent, the absorbent being characterized by the fact that, when flexed, the cuff is able to move away from the upper sheet so as to define a liquid containing region.

The operation of the absorbent article of the present invention is, in a simplified form, as follows:

- prior to use, the absorbent article is essentially flat and the lateral cuffs lay flat on the regions close to the borders of the article, substantially parallel to the surface of the upper sheet, so that between each cuff and the surface of the upper sheet, a pocket is formed (i.e. an overlapping of two substrates connected along their perimeters, except along a fraction of thereof) with a cutout facing the longitudinal central axis of the absorbent article;
- when put to use, the absorbent article assumes an anatomical arched shape and the lateral cuffs—with a minimum rigidity so as not to be distorted in a random fashion—move away from the upper sheet, tending to vertical position in relation to the original flat position. The cutout between the cuff and upper sheet opens; i.e., the region comprised between each cuff and the upper sheet is transformed into a liquid containing region ready to receive and contain arriving fluid.

In one specific embodiment, the lateral cuffs of the absorbent article of the invention are associated with a foam material, typically polyurethane foam, which offers sufficient rigidity so that the cuff may move away from the upper sheet without folding or deforming in a random fashion, to form a containing region. At the same time, the foam offers a smooth contact with the user's body without causing irritation, pain or substantial discomfort.

In another embodiment, the absorbent article of the present invention has flexible lateral wings, for instance as extensions of the upper and lower sheets, which serve to fix the article to the user's panties by folding in the region between the legs onto the external part of the panties (close to the borders of the leg openings).

In another specific embodiment, the absorbent article of the present invention has both lateral cuffs and wings which communicate with each other; i.e., the containing region formed when the absorbent article assumes an anatomical arched shape has physical continuity within the lateral wing.

Still another special characteristic of the present invention provides for containing pockets at the longitudinal ends of the absorbent article which further increases protection against leakage.

The invention will be better understood with reference to the accompanying drawings which are intentionally schematic and not necessarily drawn with respect to proportions and are provided by way of example without imposing any restriction to the scope of the invention.

DETAILED DESCRIPTION OF THE INVENTION

FIGS. 1 to 4 illustrate a particular embodiment of a intimate disposable feminine absorbent 10 which comprises an upper sheet 20, a lower sheet 30, an absorbent core 40 with side edges 90 and 100, a protective removable sheet 50 for an adhesive layer 60, a cuff 70 along side edge 90, and a cuff 80 along the opposite side edge 100.

Figure 1:
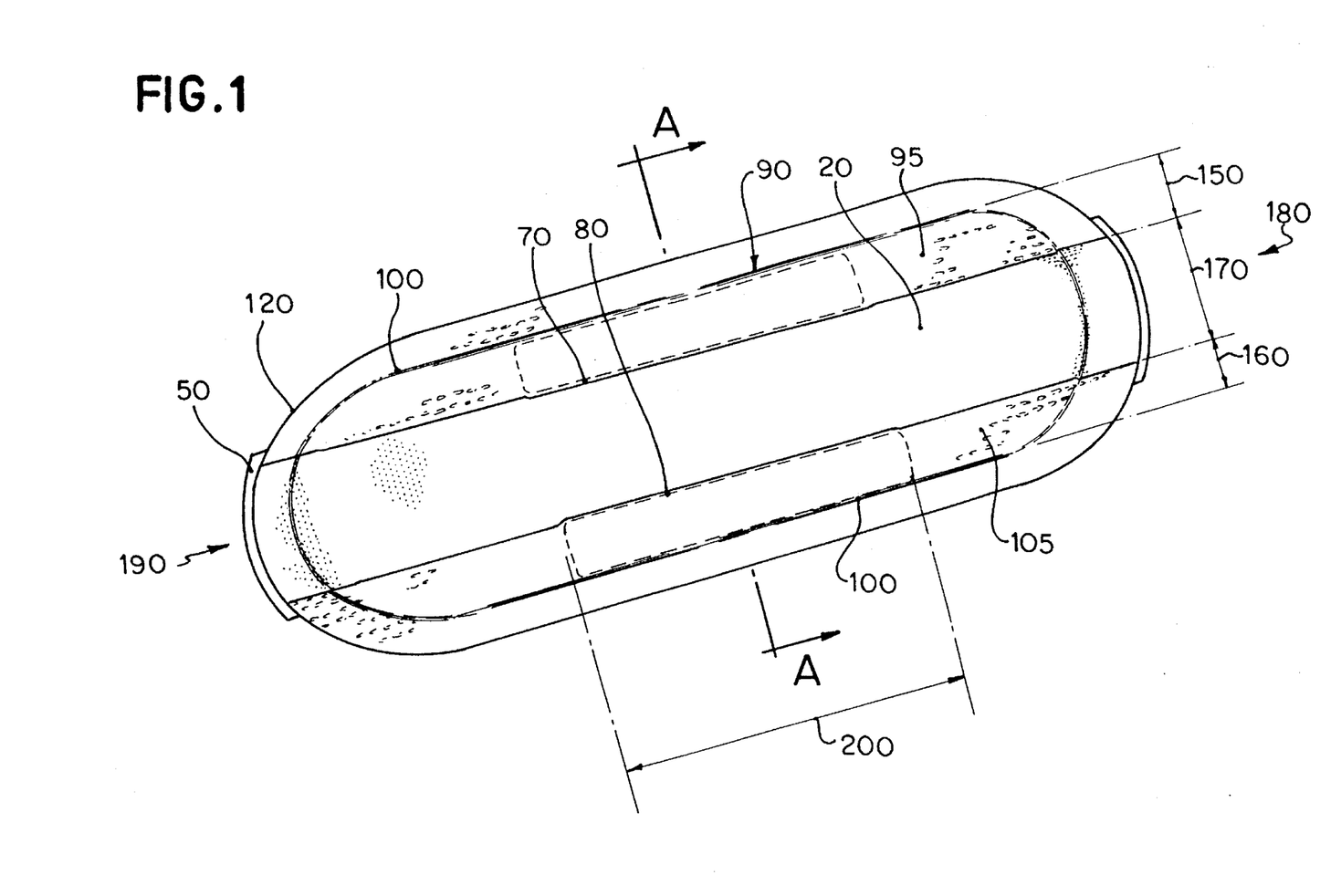
FIG. 1 is a upper view of a particular embodiment of the absorbent article according to the invention, prior to use.
Figure 2:
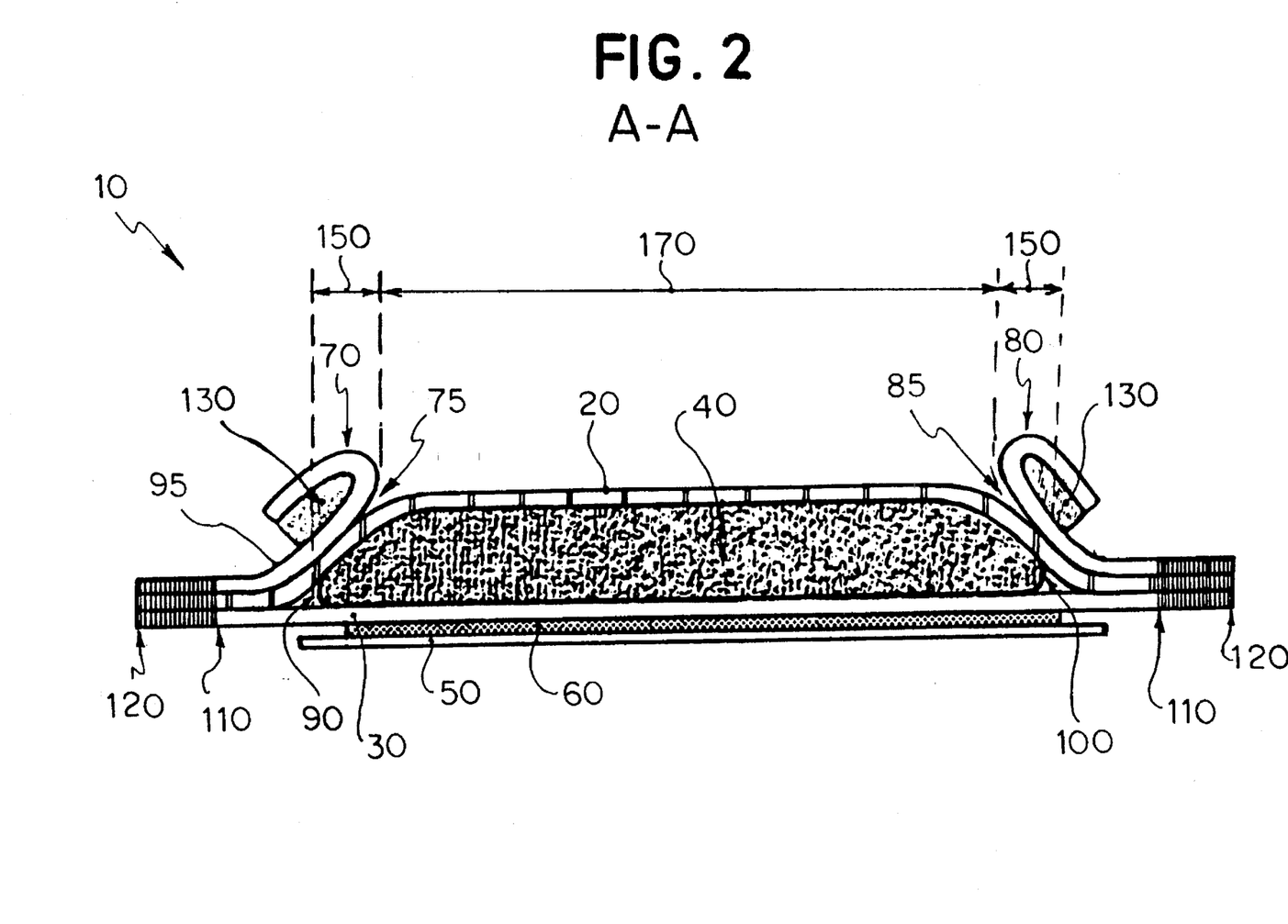
FIG. 2 shows a schematic cross section along line AA of FIG. 1.

In the present embodiment and as illustrated in FIGS. 1 and 2, between lines 110 and 120 which surround the absorbent article 10, there is a thermosealed region that circumscribes the absorbent core 40, fixing therebetween upper sheet 20, lower sheet 30, side cuff 70 (the side of edge 90) and the side cuff 80 (the side of edge 100).

In this example, cuffs 70 and 80 extend along fractions of the length of, respectively, of bands 95 and 105 of hydrophilic non-woven, along the length of the bands 95 and 105 there is preferably included soft polyurethane foam strips 130. In order to facilitate building of this embodiment, strips 95 and 105 which contain cuffs 70 and 80, are extended longitudinally from the end 180 to end 190 of the absorbent article 10. Nevertheless, strips 95 and 105 are optional and cuffs 70 and 80 may exist independently.

Along the central part 200, about 30% of the total length of absorbent core 40, in which foam strips 130 are located, cuffs 70 and 80 are only fixed between lines 110 and 120, configuring openings 75 and 85 so that they face the central longitudinal axis of the absorbent article 10.

In the regions not associated with the foam 130, strips 95 and 105 are also fixed to upper sheet 20.

As for the width of the cuffs 70 and 80, in the feature example presented, the widths 150 and 160, each one corresponds to 5% of the total width of the absorbent core 40, remaining (for the article at rest) the exposed width 170 corresponding to 90% of the total width of the absorbent core 40.

It should be observed that, when the absorbent article is not in use, cuffs 70 and 80 lay totally flat against upper sheet 20.

Figure 3:
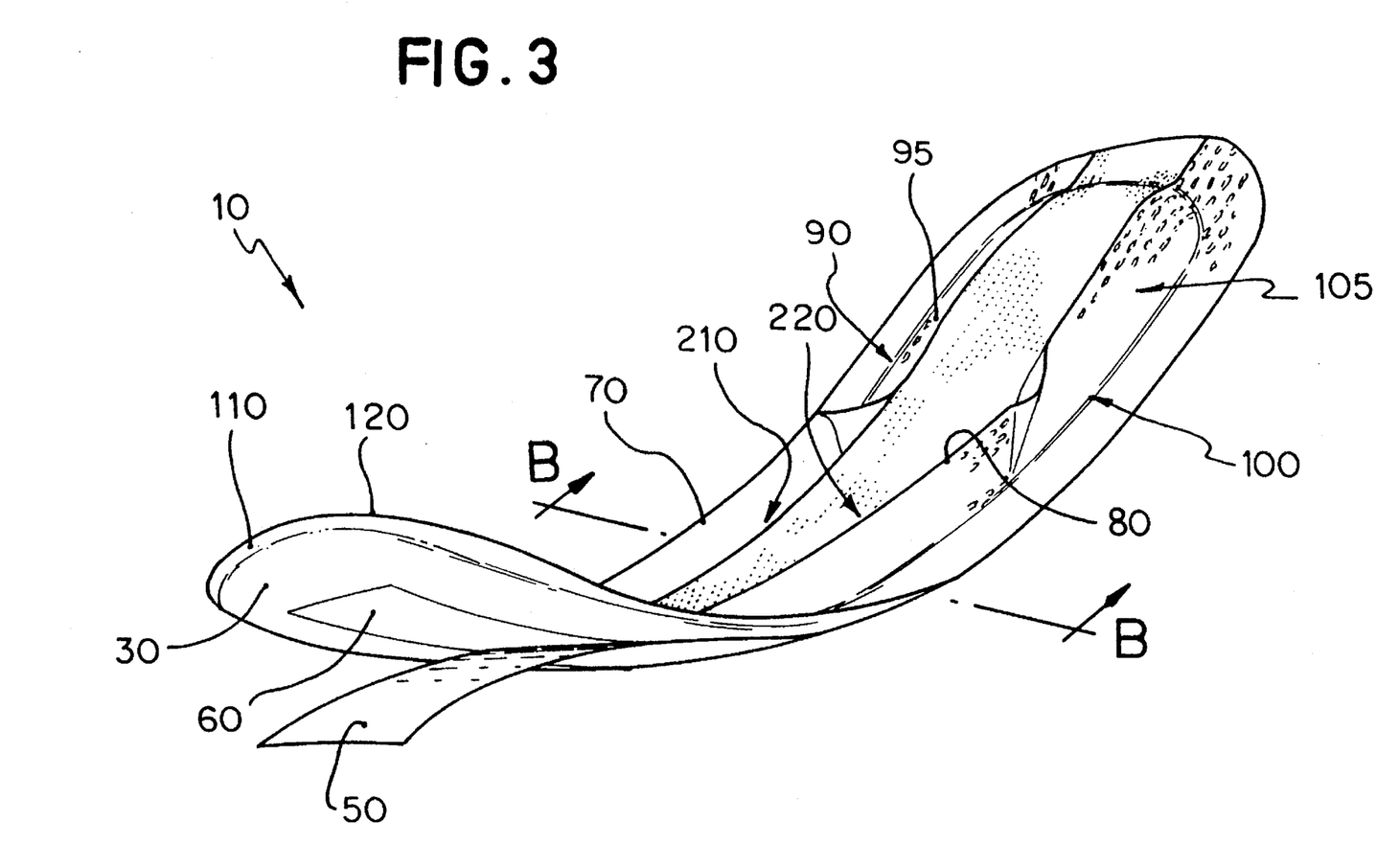
FIG. 3 shows a perspective view of the absorbent article of FIG. 1 when being put in use.
Figure 4:
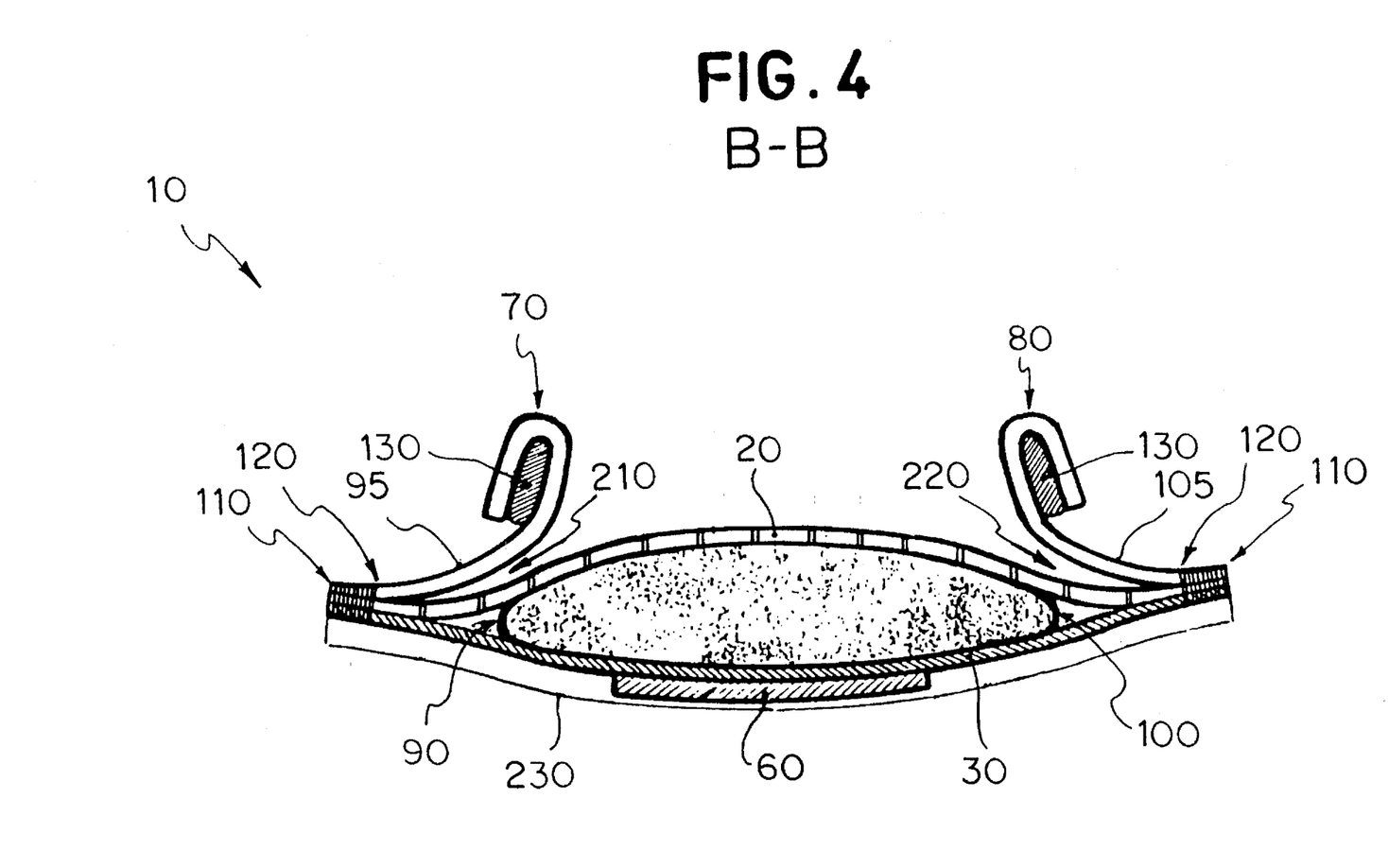
FIG. 4 shows a schematic cross section along line BB of FIG. 3.

FIGS. 3 and 4 schematically illustrate the absorbent article of the invention when placed in use, fixed to the panties 230 of the central user, assuming an anatomical arched shape. Note that along the part 200, openings 75 and 85 are created as cuffs 70 and 80 move away from upper sheet 20, pivoting in this embodiment about line 110. This causes, between upper sheet 20 and cuffs 70 and 80, the creation of containing regions 210 and 220, which are able to contain a certain volume of fluid, for example, that which is not readily absorbed through upper sheet 20 in the direction of absorbent core 40, or in addition liquid which might migrate from the inside to the outside of absorbent core 40.

Upper sheet 20 in contact with the user's pelvic region is compliant and non-irritating in contact with the skin. It is permeable to liquids permitting them to be transferred easily through its thickness. An appropriate upper sheet may be manufactured from an ample range of materials, for example, perforated plastic film, porous foam, reticulate foam, natural fiber wovens or non-wovens (as wood or cotton fibers), synthetic fibers (as polyester or polypropylene), synthetic and natural fiber combinations, etc.

Upper sheet 20 may of advantage be made of hydrophobic material, because being impermeable without being absorbent, it tends to remain dry in contact with the user's body, offering more comfort and a greater sensation of security than is provided by a hydrophilic sheet. It is preferable that upper sheet 20 comprise a perforated plastic formed film, for example as described in U.S. Pat. No. 3,929,135.

The absorbent core 40 may be any medium able to absorb and contain exudates, as well as being soft, compressible and comfortable enough not to bother the user, and non-irritant to the skin.

Absorbent core 40 may be presented be of varied dimensions and shapes, based on the performance and aesthetic needs which a person versed in the art can easily determine. It may be manufactured from an ample variety of materials, such as for example wood pulp, fibers or natural materials (for example, derived from bamboo, sugar cane husks, corn stems or cobs, peat moss, etc.), absorbent foams or sponges, synthetic fibers, polymeric fibers, super-absorbent materials (those that, when in contact with liquids, form hydrogels), any materials or combinations of absorbent materials, in mono- or multi-layers, etc.

Lower sheet 30 may be any single or combined material, which is impermeable to liquids and that is able to prevent exudates absorbed and contained in the absorbent core 40 from passing to the user's clothes or skin. Generally, it is a thin flexible plastic film, for example, polyethylene approximately 0.05 milimeters thick. Such a liquid impermeable element may be vapour permeable, for example a plastic lamina having minute pores or a liquid impermeable non-woven.

Upper sheet 20 and lower sheet 30 may optionally be of the same material, for example, a perforated plastic film which totally envelops the absorbent article of the invention.

The absorbent article 10 of the invention may even contain other layers or materials without departing from the scope of the invention. For example, it may comprise a layer of hydrophilic fibers placed between upper sheet 20 and the absorbent core 40, or even contain inside the absorbent core 40 odour absorbing particles, such as zeolites or activated carbon.

The absorbent core 40 may be fixed to its adjacent layers such as, in the embodiment being described, upper sheet 20 and lower sheet 30, by any means well known in the art, for example gluing by pulverization or adhesive lines or points. A suitable adhesive for this end is Eastobond A-3, by Eastman Chemical Products, Ohio, U.S.A.

A suitable adhesive for the fixing of some layers, for example, the upper sheet 20, the lower sheet 30 and the cuffs 70 and 80, is Findley 581 of Findley Adhesives Inc., Wisconsin, U.S.A. Such fixation may also be effected by heat sealing (i.e., by heating and the resultant softening of at least one of the polymeric materials which make up at least one of the layers) or any other appropriate means.

The removeable sheet 50 for protecting adhesive 60 has any format adequate for the protection of the such adhesive layer 60, commonly being, as in the described embodiment, a rectangular strip with its longitudinal ends rounded off, the width of which is a little wider than the width of the adhesive strip and the length of which is slightly greater than the length of the absorbent article 10, so to permit its easy removal when the absorbent article 10 is put into use. The material of removeable sheet 50 is any one suitable for the function to which it is put, i.e., to protect the adhesive strip 60 before use of the product and to be able to be removed without taking with it any substantial quantity of the protective adhesive which it protects. It is commonly kraft paper lined with silicone on the side that contacts adhesive 60.

The adhesive 60 serves as an element of fixation of the absorbent article 10 to the user's panties, and may be any, for example, an acrylic pressure sensitive adhesive, applied by spreading or pulverization, on the outer surface of the lower sheet 30, or still a double sided adhesive tape. It may be in the form of a single wide centinuous strip, several narrower continuous longitudinal or transverse strips, continuous or discontinuous lines, points, etc. Its utilization and the types of adhesives for this purpose are well known in the art.

The element of fixation of absorbent article 10 to the user's panties, adhesive strip 60 in the described embodiment, is optional and may not necessarily be present. It may also be in another form, for example, a layer of material with sufficient friction coefficient to avoid sliding of the absorbent article, applied externally to lower sheet 30, or any other equivalent known in the art. Obviously, if pressure sensitive adhesive is not used, protective sheet 50 will be unnecessary. The cuffs 70 and 80 are of any soft material which preferably does not cause irritation to the user's skin. Such material must have a minimum rigidity, sufficient to prevent random deformation when the product is put to use; the rigidity should be the minimum possible but sufficient to form opening 75 of the cuff 70 (or opening 85 of cuff 80) if it moves away from the upper sheet 20 configuring a containing region 210 (or 220). Lateral cuffs 70 and 80 may be, for example, of various overlapping layers of non-woven polymeric fibers, of plastic laminates, a coating of polyurethane foam, etc.

The rigidity of cuffs 70 and 80 does not need to conform to the description in the previous paragraph, should they be associated with another material, for example, the strip of foam 130 of the presently described embodiment. In such circumstances, the cuffs may be as flexible as desired, for example, a fine veil of non-woven material or a lamina of plastic, because the sufficient necessary rigidity will be that of the associated material or of the cuffs together with the associated material.

In this way, it is understood that any mention made herein to a cuff that has a minimum of rigidity to move away from the upper sheet 20 when the absorbent article 10 is put in use, means either that the cuff on its own has such minimum rigidity or that the cuff is associated to a material that offers, on its own or in combination, such minimum rigidity.

Any person versed in the art will be able to choose the material of cuffs 70 and 80 and any associated material, bearing in mind the following limits of rigidity:

to permit the cuff to move away from upper sheet 20 without random deformation when the article is in use; and to avoid that the lack of comfort when in contact with the user's body;

The cuffs 70 and 80 are preferably symmetrical as to shape and dimensions.

As to shape, the cuffs are preferably configured as in the feature example given and shown in FIG. 1, that is, they are strips of the same width and length. Preferably, a cuff has the width of approximately 2% to 35%, advantageously around 5% to 15%, of the width of the absorbent core 40. As to the length, preferentially, it is about 5% to 80%, advantageously, around 15% to 60% of the length of the absorbent core 40.

The fixation of the cuff 70 and 80 to the absorbent article may be of any nature provided it permits the formation of openings to define containing regions 210 and 220 when in use. Preferably, to facilitate manufacture, fixation is effected as in the described embodiment illustrated in FIGS. 1 to 4 where non-woven strips 95 and 105 are extended along each edge 90 and 100 between the ends 180 and 190, covering foam strips 130 at least along region 200. Except along region 200, where the 70 and 80 work, such non-woven strips 95 and 105 are placed or fixed by any suitable means to the surface of the sheet 20.

The hydrophilic nature of cuffs 70 and 80 may be chosen at will. Preferentially, they are hydrophilic in the internal region.

The minimum rigidity for cuffs 70 and 80 may be obtained with the utilization of various overlapping layers of non-woven material, a veil of non-woven material rolled over itself, or any other suitable means. If the cuff is associated with another material, the latter may be another type of non-woven, a cotton roll or wood pulp, a strip of foam, or any other equivalent means.

The association of cuffs 70 and 80 with other materials may assume any types and forms, without other limitations except that relate to performance and comfort. In the embodiment illustrated in FIGS. 1 to 4, a veil of non-woven material 140 is wrapped over a continuous strip 130 of foam of rectangular cross section.

Other equivalent forms of the strip 130 for this purpose are a continuous or discontinuous strip of triangular, square, circular or irregular profile, involved by or of in any other form associated with the basic material (in the given example, a non-woven material).

The associated material, in cuffs 70 and 80, may be fixed to the cuff in any adequate fashion known in the art, for example, gluing by adhesive pulverization or heat sealing.

Lateral cuffs 70 and 80 may also be associated with more than one material, forming, for example, a laminate of three layers comprising absorbent foam/non-woven/polyethylene film.

The material associated with lateral cuffs 70 and 80 may have shapes and dimensions different from the cuff itself without departing from the scope of the invention.

FIGS. 5 to 8 illustrate another embodiment of the present invention. It relates to a disposable intimate feminine absorbent 11, similar to that described with respect to FIGS. 1 to 4, comprising additionally wings 240 and 250, formed by extensions of the upper sheet 20 and of the lower sheet 40. Other differences in relation to FIGS. 1 to 4 are described below.

Figure 5:
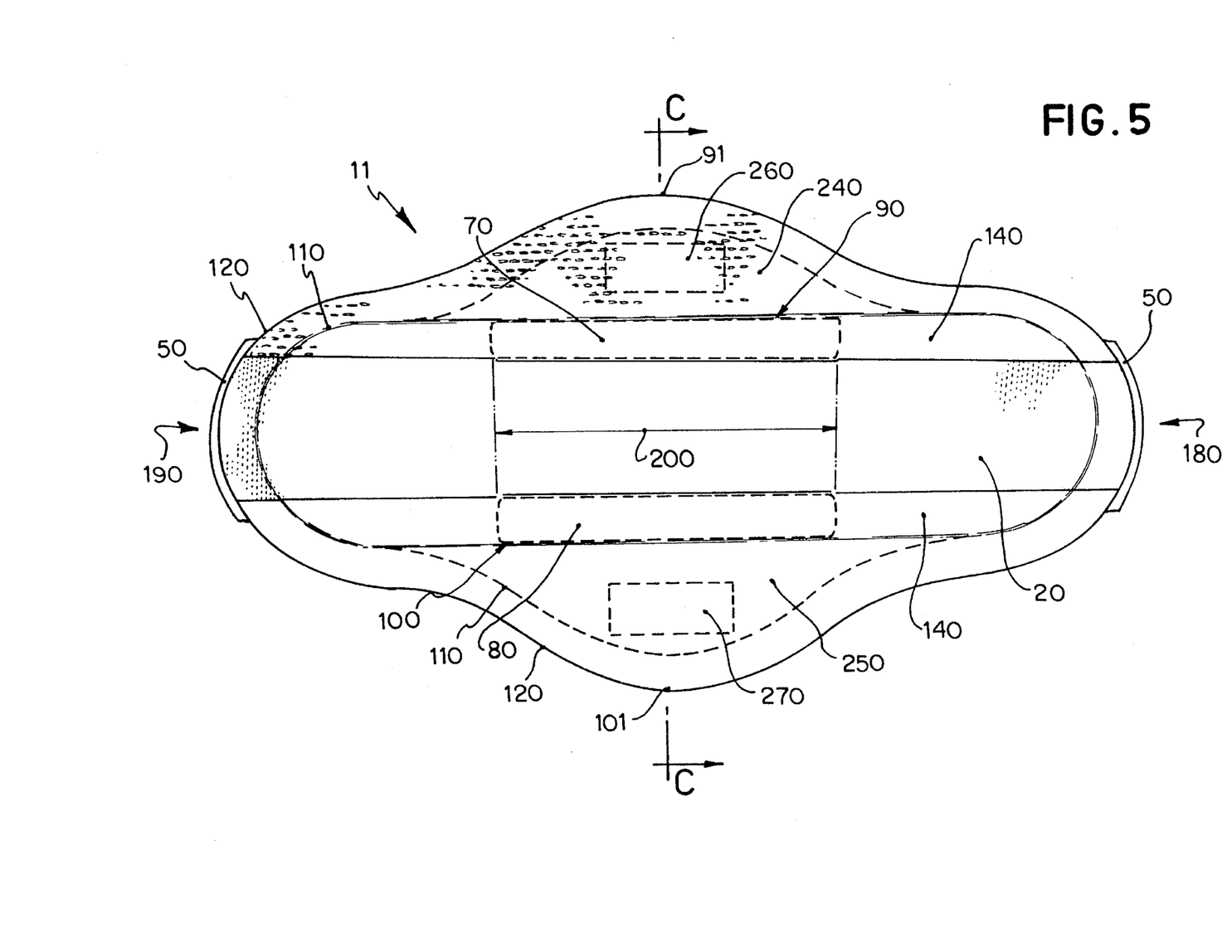
FIG. 5 shows a upper view of another special embodiment of the absorbent article of the invention, comprising lateral wings, prior to use.
Figure 6:
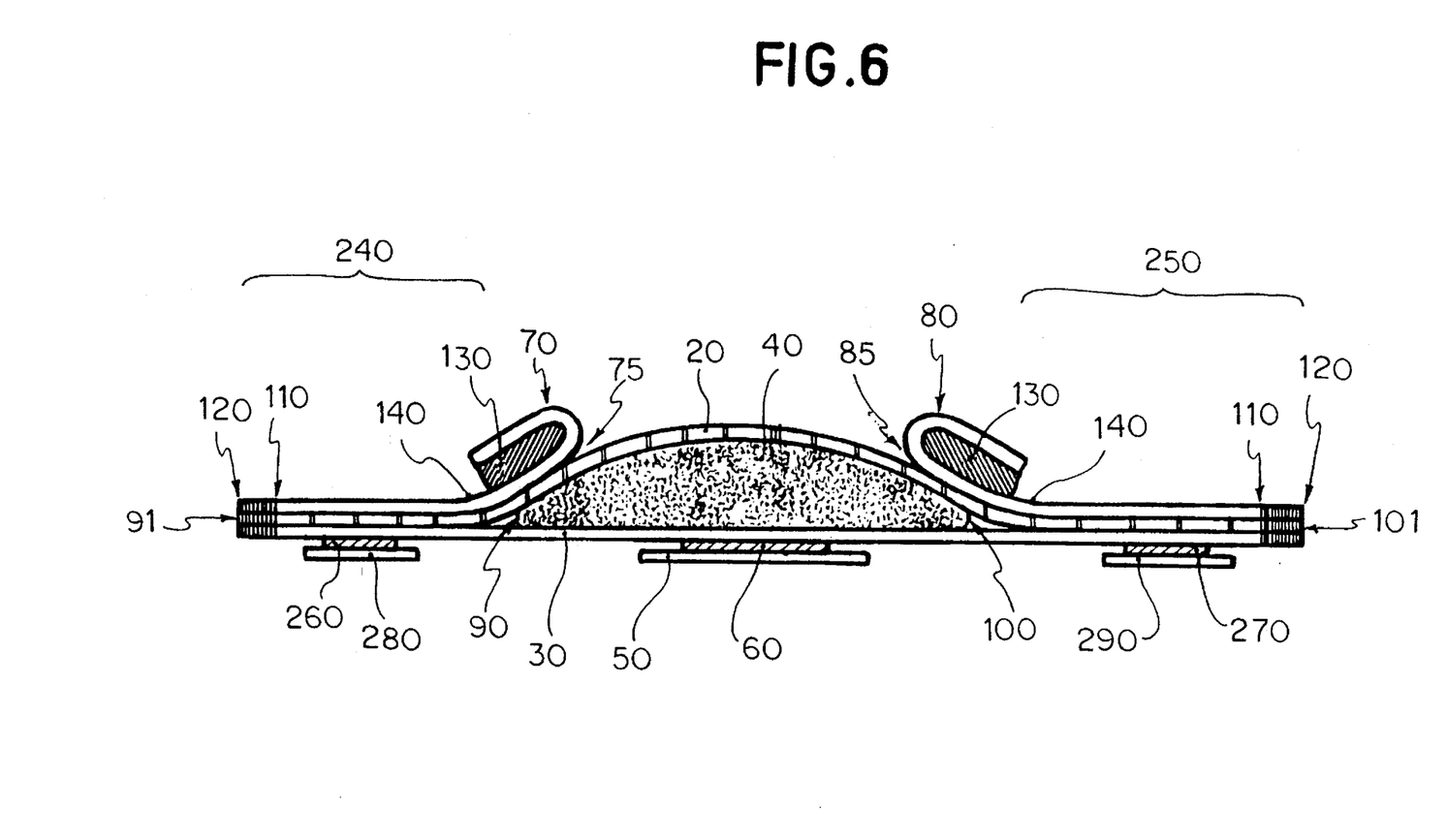
FIG. 6 is a schematic cross section along line CC of FIG. 5.

In FIGS. 5 and 6, it will be noted that the absorbent article 11, shown prior to use, is made up of a upper sheet 20, a lower sheet 30 and an absorbent core 40, removable sheets 50, 280 and 290 for protecting adhesive fixing strips 60, 260 and 270 respectively, and cuffs 70 and 80 along the edges of the absorbent core 40.

To facilitate construction, in this embodiment, the cuff 70 and 80 are fractions of the strip 140 which extend between the the longitudinal ends 180 and 190, including the surfaces of the wings 240 and 250. Strips 140 are optional and cuffs 70 and 80 may exist independently.

Cuffs 70 and 80 are associated with soft polyurethane foam strips 130. In this particular case, cuffs 70 and 80 involve or are wrapped around strips 130.

Adhesive bands 260 and 270 are "under" wings 240 and 250, that is to say, to say, applied on the external surface of the lower sheet 30.

The heat sealed region between lines 110 and 120 envelops all of article 11, including the portions of the wings 240 and 250. In this embodiment, upper sheet 20 and lower sheet 30 are fixed to each other from edge 90 (or edge 100) to the end point 91 (or 101) of wing 240 (or 250, not visible in FIG. 7). However, bands 140 of the hydrophilic non-woven, along region 200, are fixed to upper sheet 20 only in the heat sealed region between lines 110 and 120, this meaning that there is a physical continuity starting at opening 75 (or 85) in direction of end 91 (or 101). Outside region 200, the bands 140 are totally fixed to upper sheet 20.

Figure 7:
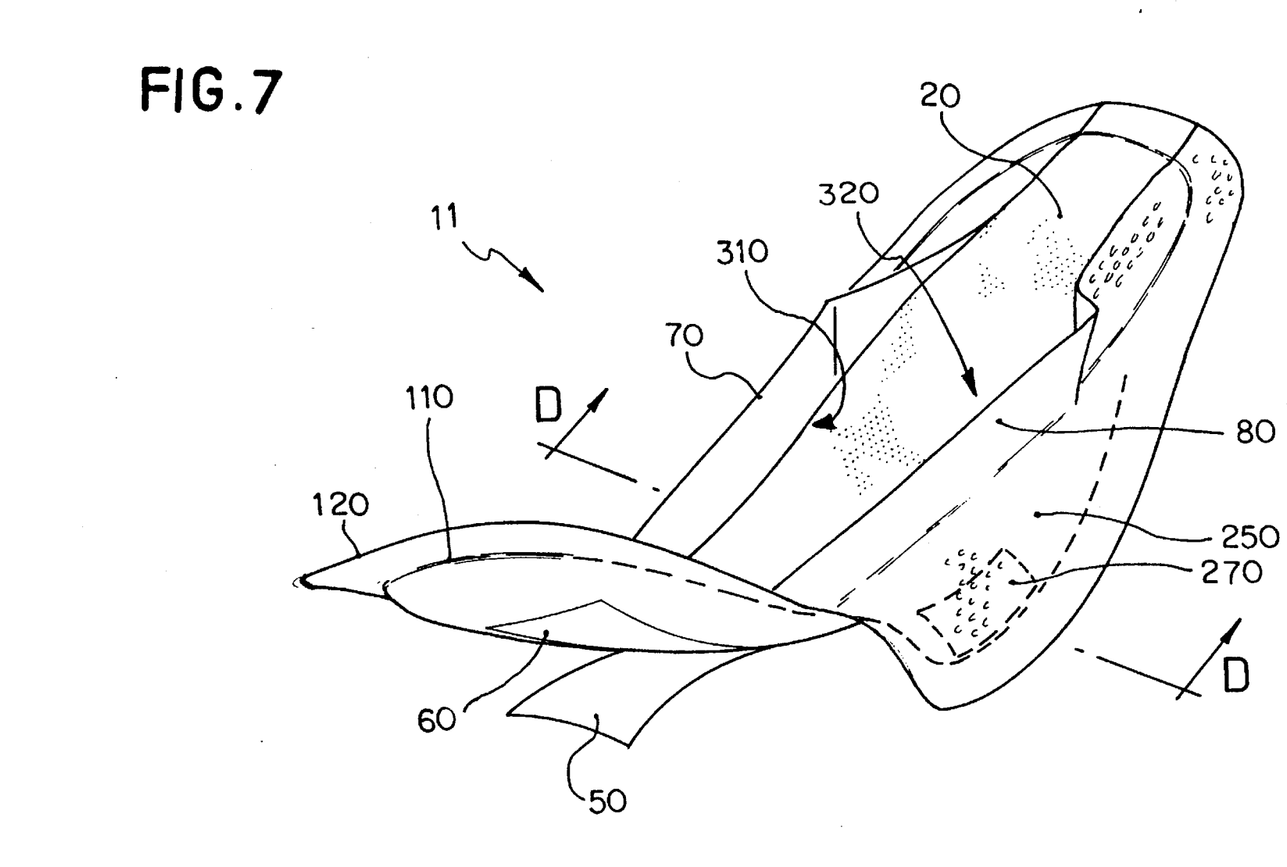
FIG. 7 is a perspective view of the article of FIG. 5 when put in use.
Figure 8:
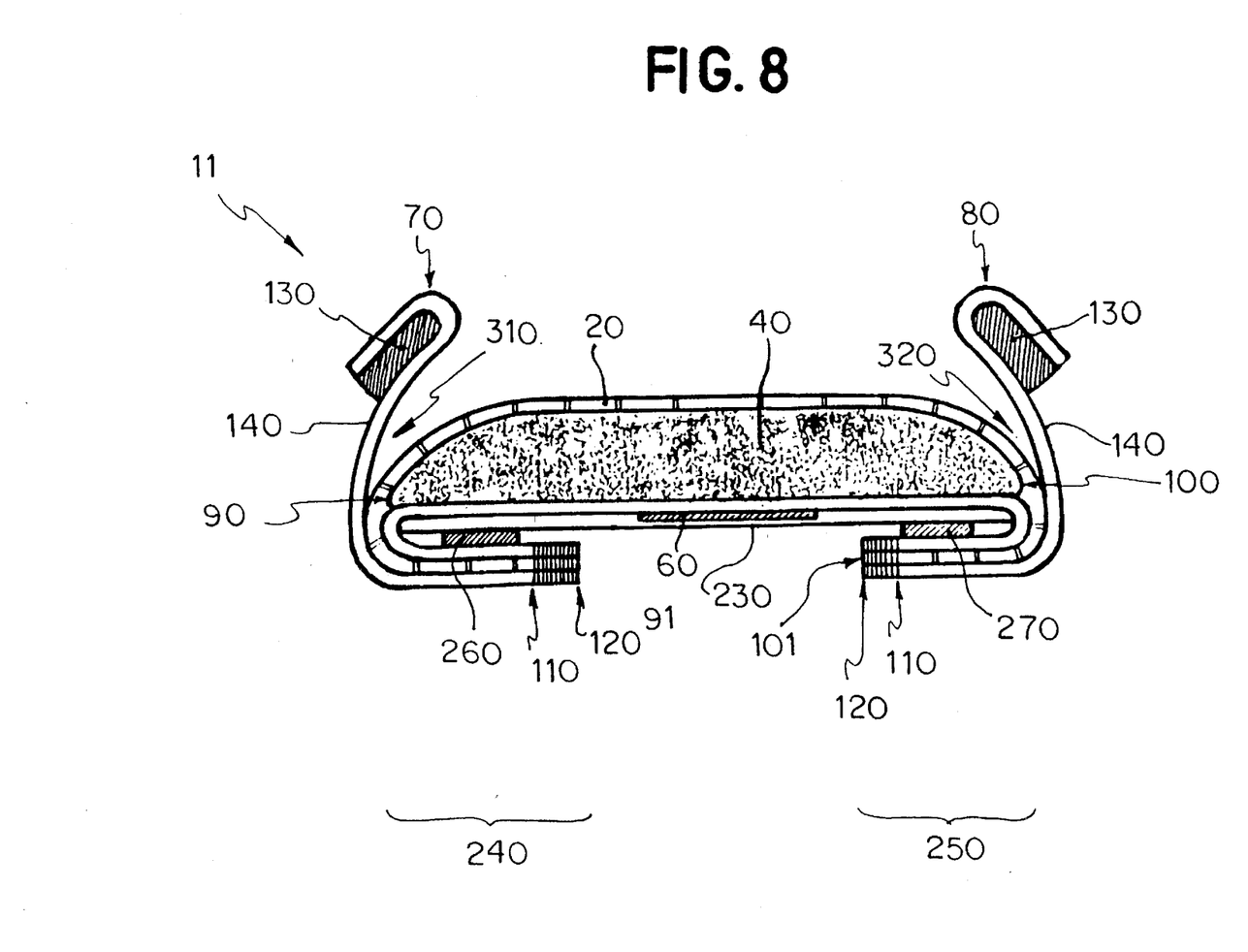
FIG. 8 shows a schematic cross section along line DD of FIG. 7.

As illustrated in FIGS. 7 and 8, the absorbent article 11 is shown in use, assuming an anatomical arched configuration. Cuffs 70 and 80 move away from upper sheet 20, and openings 75 and 85 are transformed into containing regions 310 and 320, which, in turn, in the present embodiment, have physical continuity inside the wings 240 and 250, being able to contain a substantial volume of liquid not promptly absorbed by the absorbent core 40 or even migratery from it.

Wings 240 and 250 fold toward the external part of the panties 230, folding along the lines of edges 90 and 100 in the leg openings of the panties 230, and are fixed to the crotch leg region of the same, on the side opposite to the one in contact with the lower sheet 30, by means of adhesive bands 260 and 270, after the removal of the removable protective sheets 280 and 290.

Adhesive bands 260 and 270 may have the same variations of types and shapes described for the adhesive bands 60 of FIGS. 1 to 4, including equivalent materials with a sufficient friction coefficient.

The removeable sheets 280 and 290 may have the same variations of types and shapes described for the removeable sheet 50 of FIGS. 1 to 4.

The wings 240 and 250 may or may not be extensions of the upper and lower sheets 20 and 30, including variations in that wherein they are made up of one or more materials, the same or different from those of the upper and lower sheets 20 and 30, being fixed to the former or to the latter by any means known to a person versed in the art.

Containing regions 310 and 320 may or may not have physical continuity inside wings 240 and 250. If the affirmative case, in the part in which they penetrate wings 240 and 250, they may, for example, contain absorbent material, as the type already described for the absorbent core 40, or even superabsorbent material. If not a, non-woven band 140 may, for example, be fixed on upper sheet 20 near edge 90 (or 100).

The shape and dimensions of the wings 240 and 250 may be varied, as will be known to person versed in the art, taking into account the parameters of performance and comfort. As options, the wings may have different dimensions from each other, they may be located closer to the longitudinal ends, they may be asymmetrical in relation to the absorbent article, they may be subdivided into more than one wing for each side, only one wing may be present in the absorbent article, etc..

Preferably, the absorbent article of the invention uses two symmetrical wings as illustrated in FIGS. 5 to 8, in the form of extensions of the upper and lower sheets 20 and 30.

Figure 9:
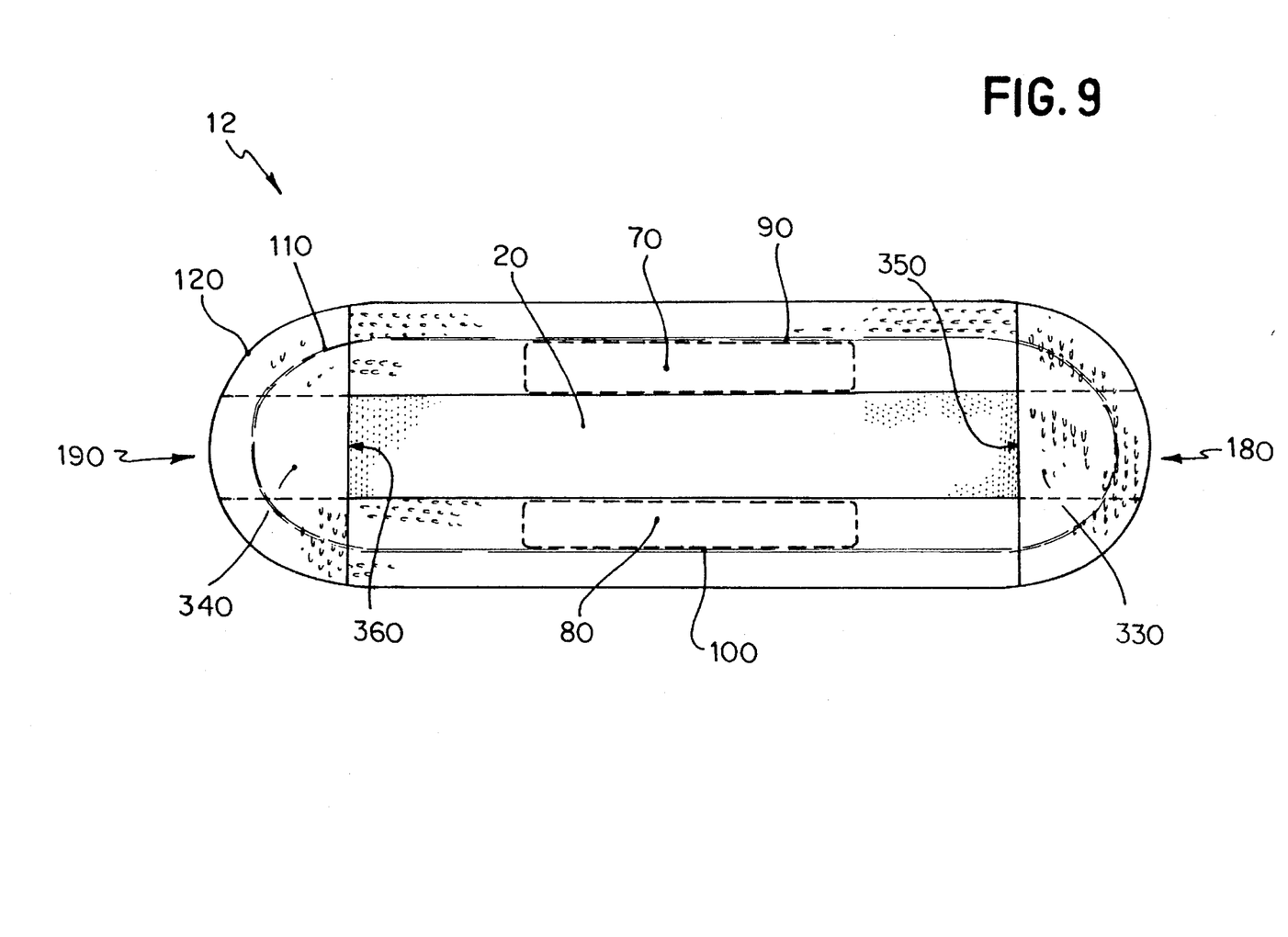
FIG. 9 shows, in perspective, another embodiment of the absorbent article of the invention, comprising cuffs of the ends, prior to use.
Figure 10:
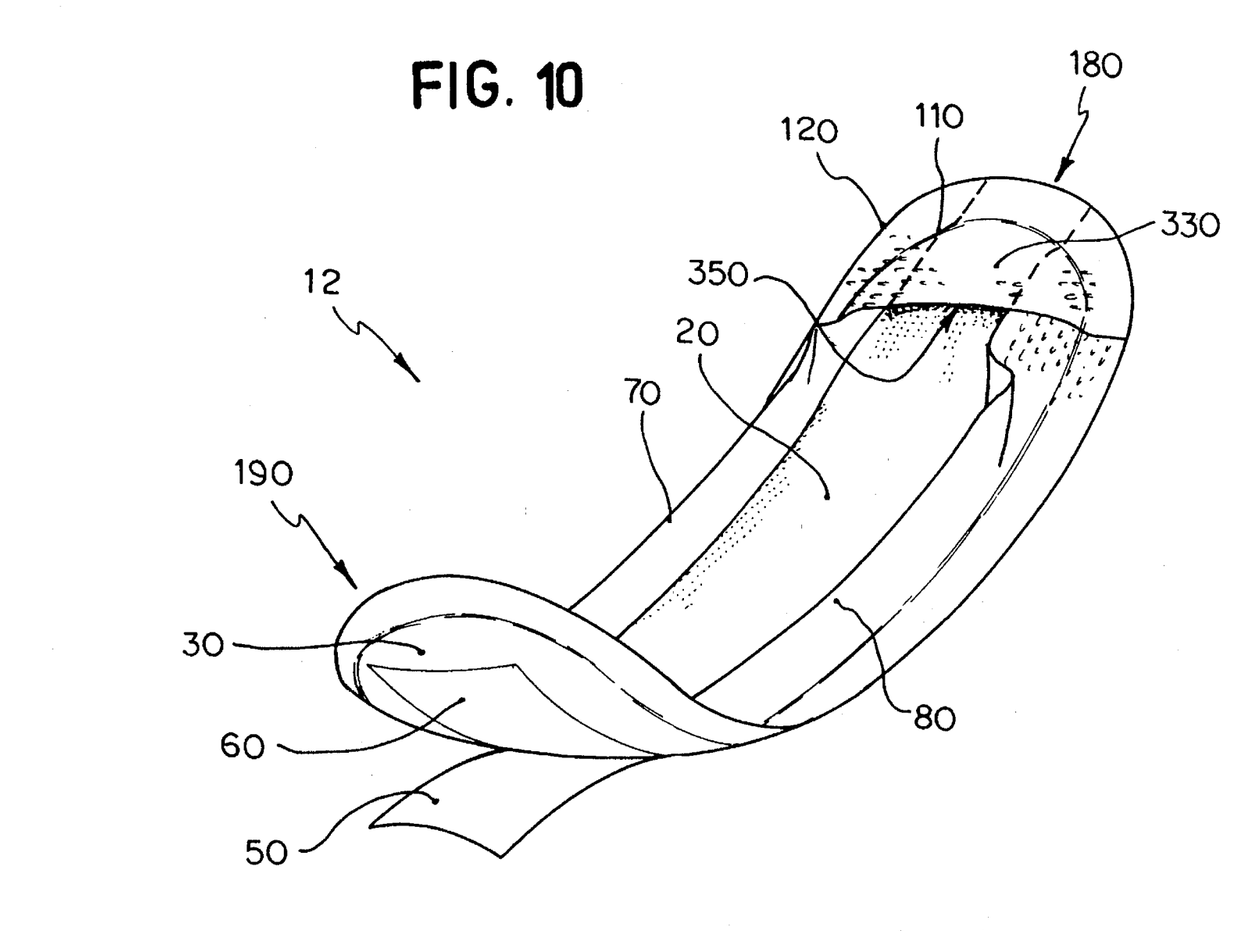
FIG. 10 shows, in perspective, the absorbent article of FIG. 9 when put into use.

Another embodiment of the present invention is shown in FIGS. 9 and 10. It comprises an absorbent article 12, corresponding to the one shown in FIGS. 1 to 4, and additionally includes end cuffs 330 and 340, useful for the case of a tendency for longitudinal leakages, for example, when the user is lying on her back or stomach.

Optionally, the product of the invention may be used with only one end cuff.

In this particular case, the cuffs 330 and 340 are a laminate of hydrophilic non-woven (on the side facing the upper sheet 20) and hydrophobic non-woven (on the opposite side), the semi-circular shape of which accompanies the contours of the ends 180 and 190, fixed on the body of article 12 by means of a heat sealed region between lines 110 and 120.

This results in a pocket being formed between this laminate and the upper sheet 20, with openings 350 and 360 which extend from edge 90 to edge 100 of the absorbent core 40, facing the central region of the absorbent article from which the liquid comes and moves towards the ends 180 and 190 of the absorbent article.

The end cuffs 330 and 340 are of shapes dimensions and materials easily determined by a person versed in the art, bearing in mind desired comfort and performance. The shape may be as described in this particular example, either as a half moon or as rectangular, triangular, irregular, etc., being fixed on upper sheet 20, on lower sheet 30 or on any suitable region. Fixing to the body of the absorbent article 12 may be by gluing, heat sealing or any equivalent.

The cuffs 330 and 340 may be extensions of the upper sheet 20 and/or of the lower sheet 30.

The material or materials of end cuffs 330 and 340 must generally be flexible and not be aggressive to the user's body.

The extension of openings 350 and 360 is preferably equivalent to the width of absorbent core 40.

Finally, it is preferable that each end cuff 330 or 340 extends along from 2% to 5% of the length of the absorbent product of the invention.

We claim:

1. Disposable intimate feminine absorbent comprising:

an upper liquid permeable sheet;

a lower liquid impermeable lining sheet;

a liquid absorbent core between said sheets;

at least one absorbent cuff comprised of a layer of hydrophilic material disposed on top of the upper liquid permeable sheet and affixed along at least one edge of said absorbent; and at least one lateral wing comprised of continuous extension of said upper liquid permeable sheet, said lower liquid impermeable sheet, and said layer of hydrophilic material;

said cuff when flexed moving away from said upper sheet to provide a region for containing liquid.

2. Disposable intimate feminine absorbent according to claim 1, in which the material of said lateral cuff is chosen from the group of hydrophilic materials comprising: non-woven materials, plastic 3. Disposable intimate feminine absorbent according to claim 1, in which said lateral cuff is comprised of more than one material.

4. Disposable intimate feminine absorbent according to claim 3, wherein said lateral cuff is comprised of a hydrophilic non-woven layer overlying a polyurethane foam core.

5. Disposable intimate feminine absorbent according to claim 1, in which said lateral cuff has between approximately 2% to around 35% of the width of said absorbent core.

6. Disposable intimate feminine absorbent according to claim 1, in which said lateral cuff has between approximately 5% to around 15% of the width of said absorbent core.

7. Disposable intimate feminine absorbent according to claim 1, in which said lateral cuff has between approximately 5% to around 80% of the length of said absorbent core.

8. Disposable intimate feminine absorbent according to claim 1, in which said lateral cuff has between approximately 15% to around 60% of the length of said absorbent core.

9. Disposable intimate feminine absorbent according to claim 1, further comprising two lateral wings.

10. Disposable intimate feminine absorbent according to claim 1, in which said lateral wing is an extension of said upper and lower sheets.

11. Disposable intimate feminine absorbent comprising:

an upper liquid permeable sheet;

a lower liquid impermeable lining sheet;

a liquid absorbent core between said sheets;

at least one absorbent cuff comprised of a layer of hydrophilic material disposed on top of the upper liquid permeable sheet and affixed along at least one edge of said absorbent; and at least one end cuff comprised of a layer of hydrophilic material overlying said upper liquid permeable sheet;

said cuff when flexed moving away from said upper sheet to provide a region for containing liquid.

12. Disposable intimate feminine absorbent according to claim 11, in which there are two end cuffs.

13. Disposable intimate feminine absorbent according to claim 11, in which said opening of said end cuff extends across the width of the said absorbent core.

14. Disposable intimate feminine absorbent according to claim 11, in which said end cuff extends along from 2% to 5% of the length of said absorbent core.

15. Disposable intimate feminine absorbent according to claim 11, in which said end cuff is provided internally with hydrophilic material and externally with hydrophobic material.

16. A sanitary napkin comprising:

an absorbent core having a body-facing side, a garment-facing side and longitudinal edges;

a liquid impermeable lower sheet overlying the body-facing side of the absorbent core;

a liquid permeable upper sheet overlying the garment-facing side of the absorbent core;

at least one lateral wing comprised of continuous extension of said upper liquid permeable sheet, said lower liquid impermeable sheet; and a pair of cuffs comprising a layer of hydrophilic material overlying the liquid permeable upper sheet and bonded thereto along the longitudinal edges, wherein when the sanitary napkin assumes a curved shape when worn and the cuffs stand up to form openings for containing liquid.

17. The sanitary napkin of claim 16, wherein the cuffs are bonded to the surface of the upper sheet inward of the longitudinal edge for at least a portion thereof.

18. The sanitary napkin of claim 16, wherein the cuffs further comprise a layer of absorbent foam.

19. The sanitary napkin of claim 16, further comprising laterally extending wings comprised of a continuous extension of the upper sheet, the lower sheet and the layer of hydrophilic material comprising the cuffs.

20. The sanitary napkin of claim 16, wherein the absorbent core has lateral ends, and further comprising a layer of hydrophilic material overlying the hydrophilic upper sheet and bonded thereto along at least a portion of the lateral ends.

* * * * *

UNITED STATES PATENT AND TRADEMARK OFFICE
CERTIFICATE OF CORRECTION

PATENT NO. : 5,490,847
DATED : February 13, 1996
INVENTOR(S) : Mauro F.C. Correa, et al.

It is certified that error appears in the above-indentified patent and that said Letters Patent is hereby corrected as shown below:

<u>IN THE CLAIMS</u>

Column 9;
    Claim 2, line 8, add <u>film and foam.</u>

Signed and Sealed this

Third Day of September, 1996

*Attest:*

BRUCE LEHMAN

*Attesting Officer*   *Commissioner of Patents and Trademarks*